United States Patent [19]

Warriner

[11] Plant 4,990

[45] Mar. 15, 1983

[54] ROSE PLANT—JACSUN

[75] Inventor: William A. Warriner, Tustin, Calif.

[73] Assignee: Jackson & Perkins Company, Medford, Oreg.

[21] Appl. No.: 298,960

[22] Filed: Sep. 3, 1981

[51] Int. Cl.[3] ..... A01H 5/00

[52] U.S. Cl. ..... Plt./8

[58] Field of Search ..... Plt./8

*Primary Examiner*—Robert E. Bagwill

*Attorney, Agent, or Firm*—Klarquist, Sparkman, Campbell, Leigh, Whinston & Dellett

[57] ABSTRACT

A miniature rose variety having a mature plant of only 2 feet in height; one-half inch long yellow buds opening to two inch diameter blooms; medium-small size foliage; and a mild, daisy-like fragrance.

1 Drawing Figure

This present invention relates to a new and distinct variety of rose plant named Jacsun of the Miniature class which was originated by me by crossing the variety Spanish Sun, U.S. Plant Pat. No. 2,809, with the variety Calgold, U.S. Plant Pat. No. 4,230.

The primary objective of this breeding was to produce a new rose variety of the Miniature class producing pure yellow blooms on a compact free blooming plant, relatively resistant to mildew. This objective was substantially achieved along with other desirable improvements as evidenced by the following unique combination of characteristics which are outstanding in the new variety and which distinguish it from its parents as well as from all other varieties of which I am aware:

1. A plant growing to only 2 feet in height.
2. Yellow buds only approximately ½ inch long opening to yellow blooms 2 inches in diameter.
3. Medium size to small foliage.
4. Good resistance to rose powdery mildew.
5. A mild, daisy-like, fragrance.

Asexual reproduction of this new variety by rooting cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with the Royal Horticultural Society Colour Chart except where ordinary dictionary significance of color is indicated.

Parentage:

*Seed parent.*—Spanish Sun, U.S. Plant Pat. No. 2,809.

*Pollen parent.*—Calgold, U.S. Plant Pat. No. 4,230.

Classification:

*Botanical.*—Rosa hybrid.

*Commercial.*—Miniature.

FLOWER

Observations made from specimens grown at Irvine, Calif., in August 1981.

Blooming habit: Continuous.

Bud:

*Size.*—½" to ⅝" when petals start to unfurl.

*Form.*—Long, pointed.

*Color.*—When sepals first divide, Yellow 15B; when half blown, upper side of petals Yellow 15C; lower side of petals Yellow 15C.

*Sepals.*—Color: Outer surface Green 138B; three appendaged sepals lightly appendaged; two unappendaged sepals hairy edge.

*Receptacle.*—Color: Green 138B. Shape: bowl. Size: Large, broad. Surface: smooth.

*Peduncle.*—Length: Short. Surface: Hairy. Color: Light green. Strength: Stiff, erect.

*Opening.*—Petals roll back, slightly quilled in full open stage.

Bloom:

*Size.*—Small. Average open size 2".

*Borne.*—In clusters, irregular.

*Stems.*—Short, strong.

*Form.*—When first open, flat. Permanence: Outer petal edges slightly curled.

*Petalage.*—Number of petals under normal conditions: 25–30.

*Color.*—Center of flower: Upper side of petals Yellow 15C. Reverse side of petals Yellow 15C. Base of petals Yellow 15C. General tonality from a distance: Yellow 15C.

*Discoloration.*—General tonality at end of first day, Yellow 15C; third day, very little fading.

*Fragrance.*—Slight, daisy-like.

Petals:

*Texture.*—Thick.

*Shape.*—Oval.

*Form.*—Tips slightly recurved; edges slightly quilled.

*Arrangement.*—Informal. Petaloids: Few.

*Persistence.*—Drop off cleanly.

*Lastingness.*—On the plant, long. As cut flowers, long.

Reproductive parts:

*Anthers.*—Large. Color: Yellow/Orange. Arrangement: Regular around styles.

*Filaments.*—Color: Yellow.

*Pollen.*—Gold yellow.

*Styles.*—Purplish red.

*Stigmas.*—Color: Yellow.

PLANT

Form: Bush.

Growth: Vigorous, dwarf, compact grows 18" to 24".

Foliage:

*Number of leaflets on normal mid-stem leaves.*—5 or 7.

*Size.*—Small.

*Quantity.*—Normal.

*Color.*—New foliage: Green 137C. Old foliage: Green 137A.

Leaflets:

*Shape.*—Oval pointed.

*Texture.*—Upper side: Smooth.

*Edge.*—Serrated.

*Serration.*—Single, small.

*Petiole.*—Rachis: Color, green. Underside: Large prickles. Upper edge with many stipitate glands.

*Stipules.*—Long.

*Disease resistance.*—Resistant to mildew, blackspot, under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalk, ordinary.

*Form.*—Oval base. Long, hooked downward slightly.

*Color when young.*—Green.

*Position.*—Irregular.

Small prickles:

*Quantity.*—On main stalks, none. On laterals, none.

I claim:

1. A new and distinct variety of rose plant of the miniature class, substantially as herein shown and described, characterized particularly as to novelty by the unique combination of compact plant, yellow buds and blooms, small foliage that is resistant to mildew and a mild daisy-like fragrance.

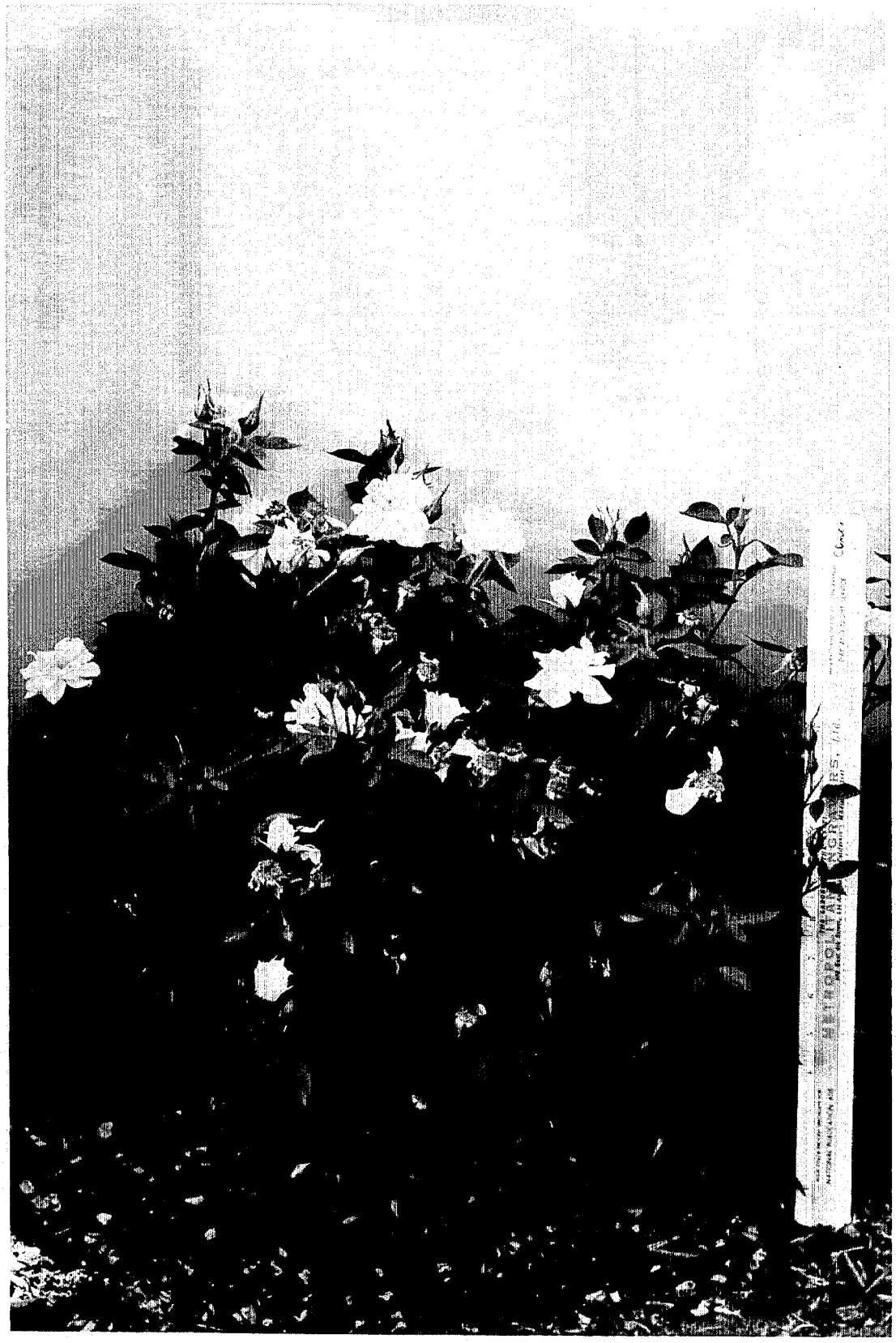

* * * * *